(12) United States Patent  (10) Patent No.: US 7,005,858 B1
Luo  (45) Date of Patent: Feb. 28, 2006

(54) SYSTEM AND METHOD FOR DECREASING ESD DAMAGE DURING COMPONENT LEVEL LONG TERM TESTING

(75) Inventor: Jih-Shiuan Luo, San Jose, CA (US)

(73) Assignee: Hitachi Global Storage Technologies Netherlands, B.V., Amsterdam (NL)

( * ) Notice: Subject to any disclaimer, the term of this patent is extended or adjusted under 35 U.S.C. 154(b) by 0 days.

(21) Appl. No.: 10/949,998

(22) Filed: Sep. 23, 2004

(51) Int. Cl.
*G01N 27/60* (2006.01)
*H02H 9/00* (2006.01)

(52) U.S. Cl. .................. 324/452; 324/457; 324/158.1; 361/56; 361/58

(58) Field of Classification Search ........ 324/750–765, 324/158.1; 360/323; 361/56, 111
See application file for complete search history.

(56) References Cited

U.S. PATENT DOCUMENTS

| | | | | |
|---|---|---|---|---|
| 4,823,088 | A | * | 4/1989 | Fukuda ........................ 324/456 |
| 5,132,612 | A | * | 7/1992 | Burns et al. ................. 324/755 |
| 5,465,186 | A | | 11/1995 | Bajorek et al. ............. 360/113 |
| 6,373,660 | B1 | | 4/2002 | Lam et al. ................ 360/234.5 |
| 6,377,411 | B1 | | 4/2002 | Katsumata et al. ........... 360/46 |
| 6,442,009 | B1 | * | 8/2002 | Kameda et al. ............... 361/56 |
| 6,538,857 | B1 | | 3/2003 | Doss et al. .................. 360/323 |
| 6,556,409 | B1 | * | 4/2003 | Chittipeddi et al. ......... 361/111 |
| 6,574,078 | B1 | * | 6/2003 | Voldman ..................... 360/323 |
| 2003/0235019 | A1 | | 12/2003 | Ker et al. ..................... 361/56 |

* cited by examiner

*Primary Examiner*—Vinh Nguyen
*Assistant Examiner*—Emily Y Chan
(74) *Attorney, Agent, or Firm*—Larry B. Guernsey; Intellectual Property Law Offices

(57) ABSTRACT

A method is disclosed for minimizing damage from electrostatic discharge (ESD) during long-term testing of electronic components and assemblies. The method includes conducting a stress-test, during which a protection circuit is engaged, which shields components and assemblies from ESD. Then at least one functional test is conducted, at which time, the protection circuit is disengaged.

Also disclosed is a system for conducting long-term testing of electronic components and assemblies while providing protection from ESD. The system includes a testing circuit for providing current to the components and assemblies during the long-term testing which includes at least one stress-testing phase and at least one functional testing phase. Also included is a protection circuit for protecting the components and assemblies during said stress-testing phase of said long-term testing. A switch is included for disengaging the protection circuit from the components and assemblies during said functional testing phase of said long-term testing.

17 Claims, 4 Drawing Sheets

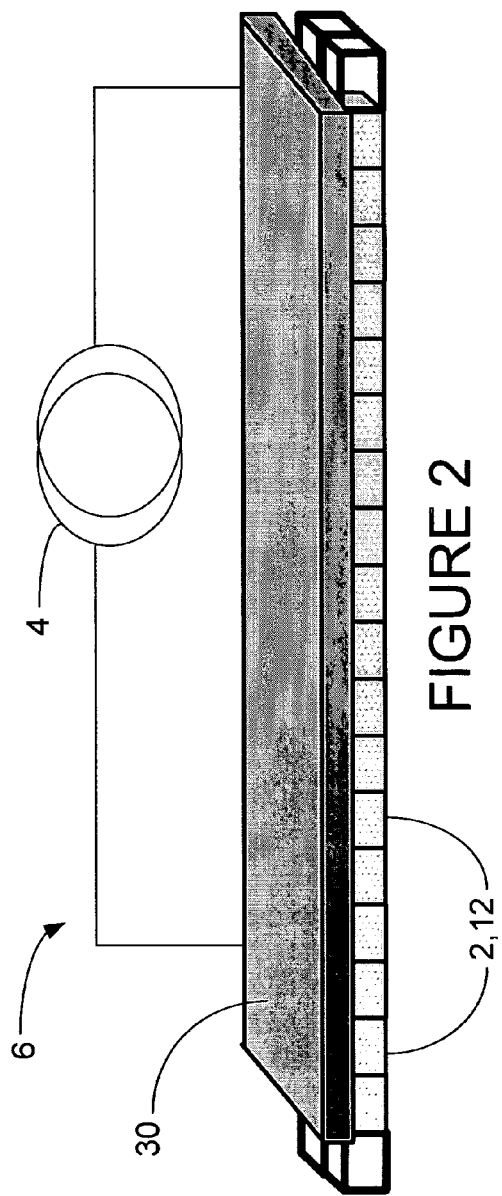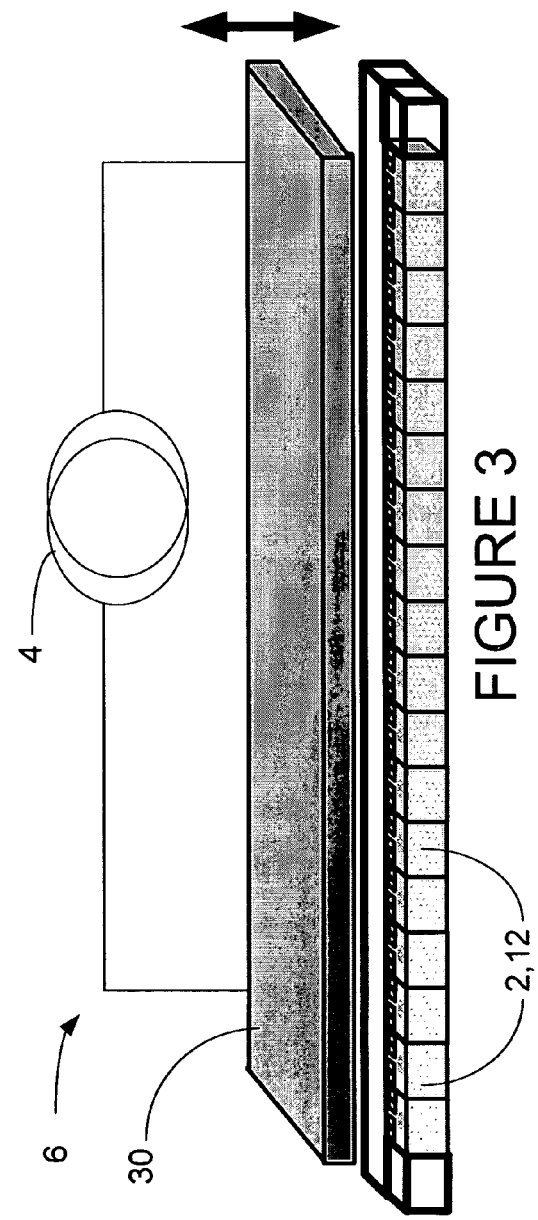

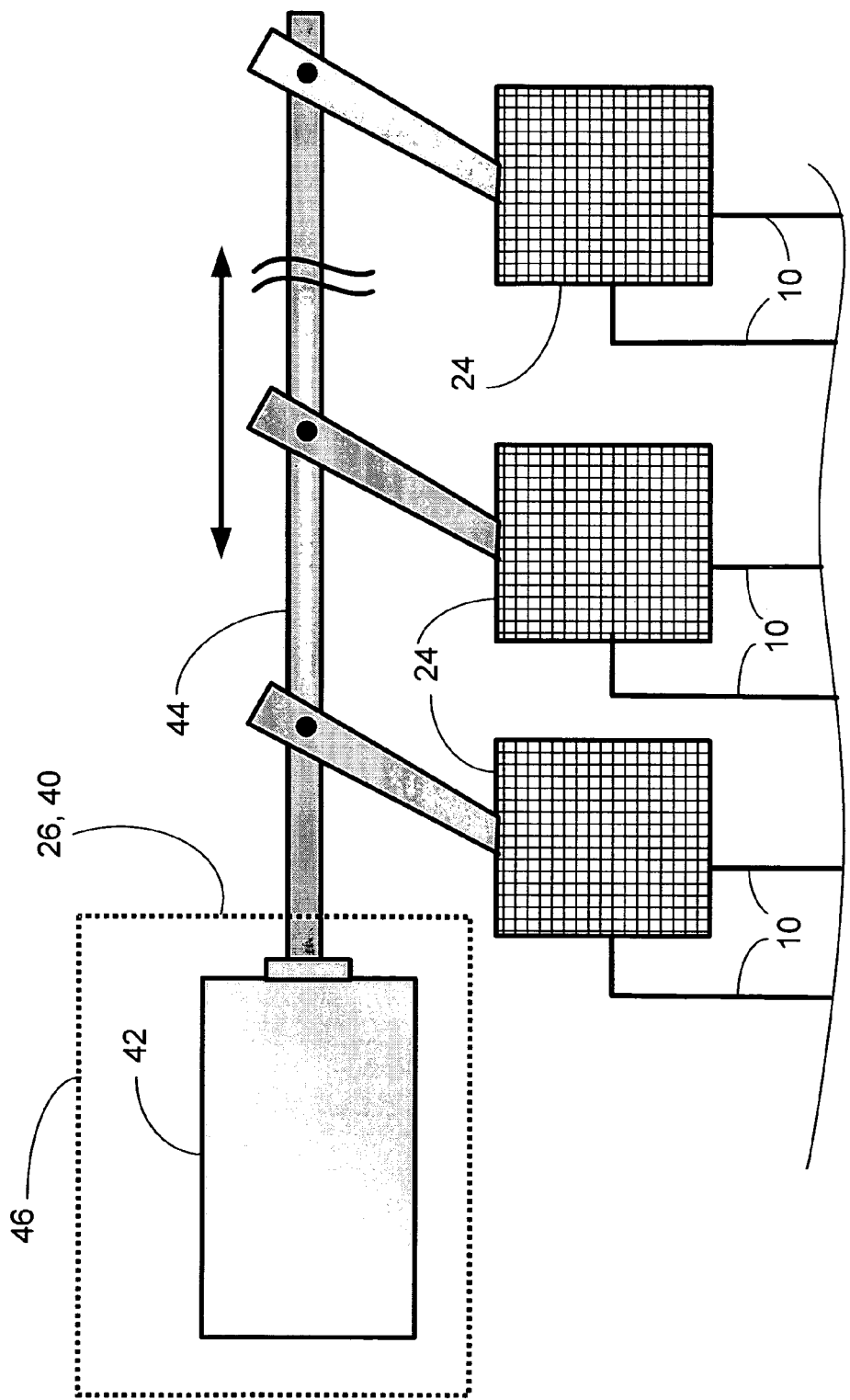

SYSTEM AND METHOD FOR DECREASING ESD DAMAGE DURING COMPONENT LEVEL LONG TERM TESTING

BACKGROUND OF THE INVENTION

1. Field of the Invention

The present invention relates generally to long-term testing of components and more particularly to protecting components from Electrostatic discharge (ESD) during long-term testing.

2. Description of the Prior Art

Long-term testing has become more and more important as competition in the electronics field becomes ever more intense. A company's reputation for reliability is a major factor in many customers' purchasing decision. Reliability, in turn, comes largely from improved procedures based on data gathered during long-term testing of components. During these long-term tests, manufacturers can gather important information on modes of failure, and specific component performance, which can provide valuable feedback to improve devices and components.

Unfortunately, long-term testing can expose components to damage from electrostatic discharge (ESD, here ESD is inclusive of discharge events resulting from electromagnetic interference (EMI), for example), that is generated in amounts not possible during realistic everyday operation by the consumer. In order to avoid damaging components during testing, it is important to protect components from ESD.

ESD can occur when sparks or electrical discharge jump from electrically charged objects to an approaching conductive object. ESD can be generated in many ways, such as by friction between surfaces of moving or rotating objects. In particular, it has been well known that assemblers or production personnel who shuffle their feet while walking across rugs may generate a static charge that can damage components. The use of grounding straps has therefore been common for assemblers in the electronics industry.

Production machinery itself may produce static charge. The present inventor has found that even so common an act as the switching on of a Xenon lamp in the testing facility has produced ESD which lead to puzzling failures before the source of damage was discovered.

Disk drive heads are often damaged due to ESD during a long term thermal or other reliability testing. The test may run as long as 1000 hours and it is difficult to keep the heads from any source of ESD for such long time. Possible solutions that have been proposed to protect the heads include the use of back-to-back diodes, and capacitors in parallel. Unfortunately, diodes provide protection only up to 700 mV but disk heads generally are destroyed if 700 mV is applied in 1 nS or longer time constant. Higher values of capacitance provide higher-level protection under fast transitions in the nanosecond range, but a higher value of capacitance also slows down the speed for Quasi-Static measurements in which uniformed fields are applied to each head/device for magnetic performance evaluations. In addition, capacitors offer essentially no protection from slow transients.

Thus there is a need for a system for long term testing of electronic components and devices which allows for production of realistic performance data without exposing components and devices to damage from ESD.

SUMMARY OF THE INVENTION

A preferred embodiment of the present invention is a system and method for minimizing damage from electrostatic discharge (ESD) during long-term testing of electronic components and assemblies. The method includes conducting a stress-test, during which a protection circuit is engaged, which shields said components and assemblies from ESD. Then at least one functional test is conducted during said stress-test, at which time the protection circuit is disengaged.

Also disclosed is a system for conducting long-term testing of electronic components and assemblies while providing protection from ESD. The system includes a testing circuit for providing current to the components and assemblies during the long-term testing which includes at least one stress-testing phase and at least one functional testing phase. Also included is at least one protection circuit for protecting the components and assemblies during said stress-testing phase of said long-term testing. A switch is included for disengaging the protection circuit from the components and assemblies during said functional testing phase of said long-term testing.

It is an advantage of the present invention that electrical components and assemblies can be given long-term testing without producing excessive failures which produce unnecessarily low production reliability projection.

It is another advantage of the present invention that higher quality, more durable products can be produced.

It is yet another advantage of the present invention that electronic components and assemblies can be protected from ESD, yet still give accurate and reliable testing results during functional testing.

It is still another advantage of the present invention that improved two-stage testing may be practiced without subjecting components and assemblies to unrealistic levels of ESD.

These and other features and advantages of the present invention will no doubt become apparent to those skilled in the art upon reading the following detailed description which makes reference to the several figures of the drawing.

IN THE DRAWINGS

The following drawings are not made to scale as an actual device, and are provided for illustration of the invention described herein.

FIG. 2 is an isometric detail view of a probe card as used in a system for testing an array of electronic components, the probe being in a downward position to engage the components;

FIG. 3 is an isometric detail view of a probe card as used in a system for testing an array of electronic components, the probe being in a upward position to disengage the components;

FIG. 5 is a side detail view of an actuator connected to a number of mechanical switches to engage and disengage from a number of protection circuits.

DETAILED DESCRIPTION OF THE PREFERRED EMBODIMENTS

Figure 1:
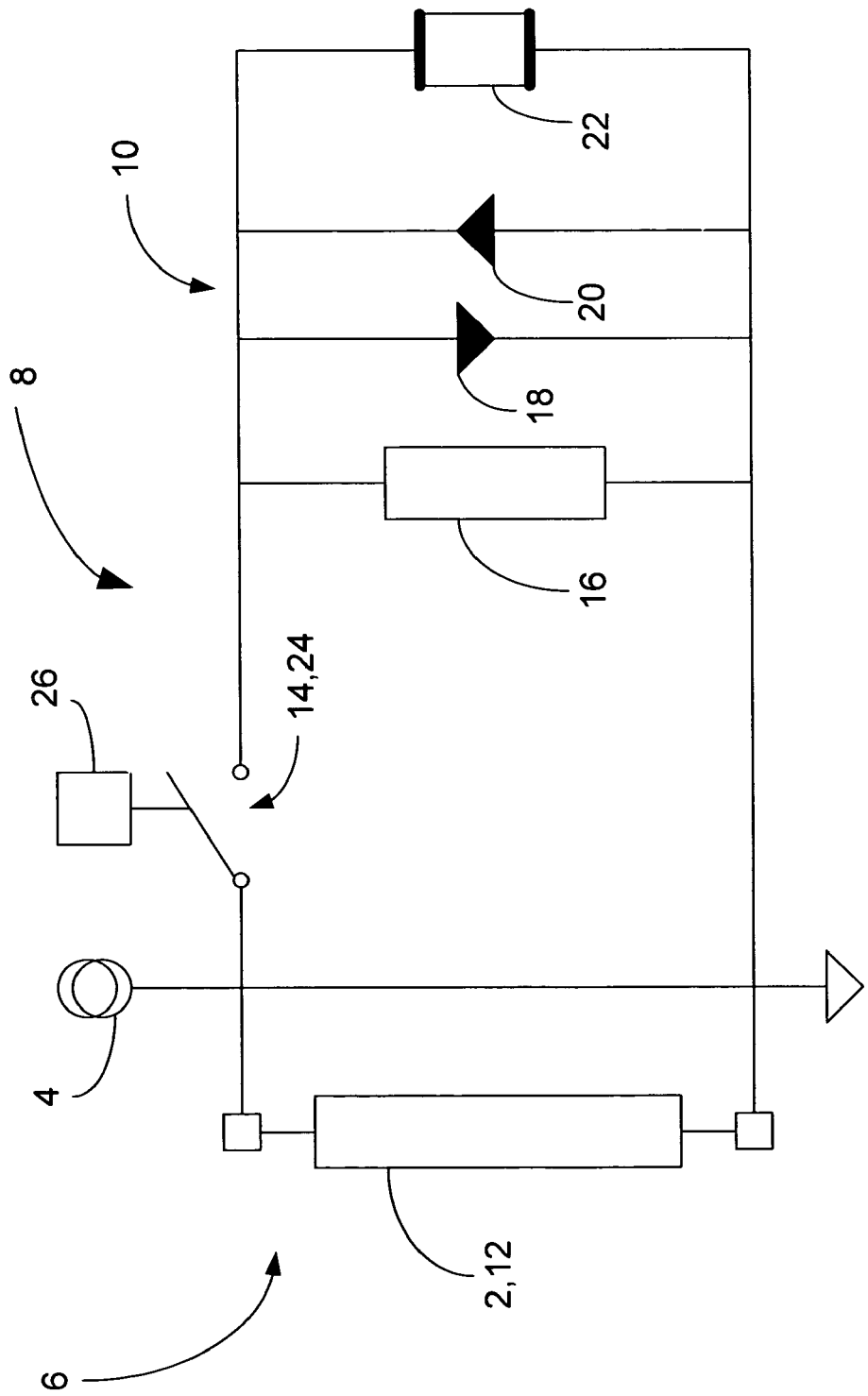
FIG. 1 is a schematic diagram of a system for testing electronic components with a circuit for protection from ESD damage.

As discussed above, ESD can occur when sparks or electrical discharge jumps from electrically charged objects to an approaching conductive object. ESD can be generated in many ways, such as by friction between surfaces of moving or rotating objects. In particular, it has been well known that assemblers or production personnel who shuffle their feet while walking across rugs may generate a static charge that can damage components. The use of grounding straps has therefore been common for assemblers in the electronics industry.

Production machinery itself may produce static charge. The present inventor has found that even so common an act as the switching on of a Xenon lamp in the testing facility has produced ESD which lead to puzzling failures before the source of damage was discovered.

As commonly practiced in the industry currently, long-term testing is performed in two stages, namely stress tests, and functional tests. Stress tests are designed to apply electrical and temperature stress to each component or assembly of components. Functional testing is used to evaluate performance of the component or assembly at the end of each cycle of stress testing. For ease of reference, this type of testing utilizing stress testing and functional testing will be referred to as "two-stage testing".

The system and method disclosed here may be particularly utilized for the testing of magnetic read heads of hard disk drives, and the discussion below will use this application as an example for discussion. However, it should be understood that this same system and method can be used for a number of other applications and components, and the example of magnetic read heads should not be taken as a limitation on the use of the present method and system. It is to be understood that one skilled in the art would find the present system and method to be applicable to nearly any component or system of components in which two-stage long-term testing is used.

Disk drive heads are often damaged due to ESD during a long term thermal or other reliability testing. The test may run as long as 1000 hours and it is difficult to keep the heads from any source of ESD for such long time. Possible solutions that have been proposed to protect the heads include the use of back-to-back diodes, and capacitors in parallel. Unfortunately, diodes provide protection only up to 700 mV but disk heads generally are damaged if 700 mV is applied in 1 nS or longer time constant. Higher values of capacitance provide higher-level protection under fast transitions in the nanosecond range, but a higher value of capacitance also slows down the speed for Quasi-Static measurements in which uniformed fields are applied to each head/device for magnetic performance evaluations. In addition, capacitors offer essentially no protection from slow transients.

The present invention takes another approach which provides ESD protection without sacrificing measurement efficiency. Generally, the present invention uses a two-part methodology: (1) Read heads are shunted during long-term stress measurements and (2) The shunting circuit is disconnected during Quasi-Static measurements.

During the first phase, which involves stress-testing, a bias current is applied to each individual head. A protection circuit (controlled by computer automation) is connected, which is generally a shunting circuit in parallel with the read heads for ESD protection. With the shunting circuit in place, the bias voltage or current through the read head is identical to that without the shunting circuit.

During the second phase, the shunting circuit is disconnected from the read heads every time Quasi Static Measurement is performed.

A system 8 including a testing circuit 6 and a detailed protection circuit 10 is shown in FIG. 1 for testing electronic components 12. It is to be understood that these components can be of many types and varieties, but for the purposes of this discussion, it will be assumed that they are disk drive sliders 2. A current source 4 in the testing circuit 6 applies current to the components 12 and the protection circuit 10 is connected during the stress testing cycle to protect the components from ESD damage and is then disconnected from the components 12 during Quasi Static Measurement testing. The protection circuit 10 includes a switch 14 for connecting to and disconnecting from the sliders 2, a resistor 16 that is about 10 ohm for 5× protection, back-to-back diodes 18, 20, in which the preferred clamping voltage around 400 mV or for SiGe diodes, the lowest voltage is approximately 500 mV, and capacitor 22 with a preferred value of about 1nF. It is important that preferably a mechanical switch 24 is used in the protection circuit 10 because electromagnetic relay switches often introduce electrical transients into the electronic components 12 and cause damage. For this reason, it is preferred that a mechanical switch 24 operated by external actuator 26 is used.

Figure 4:
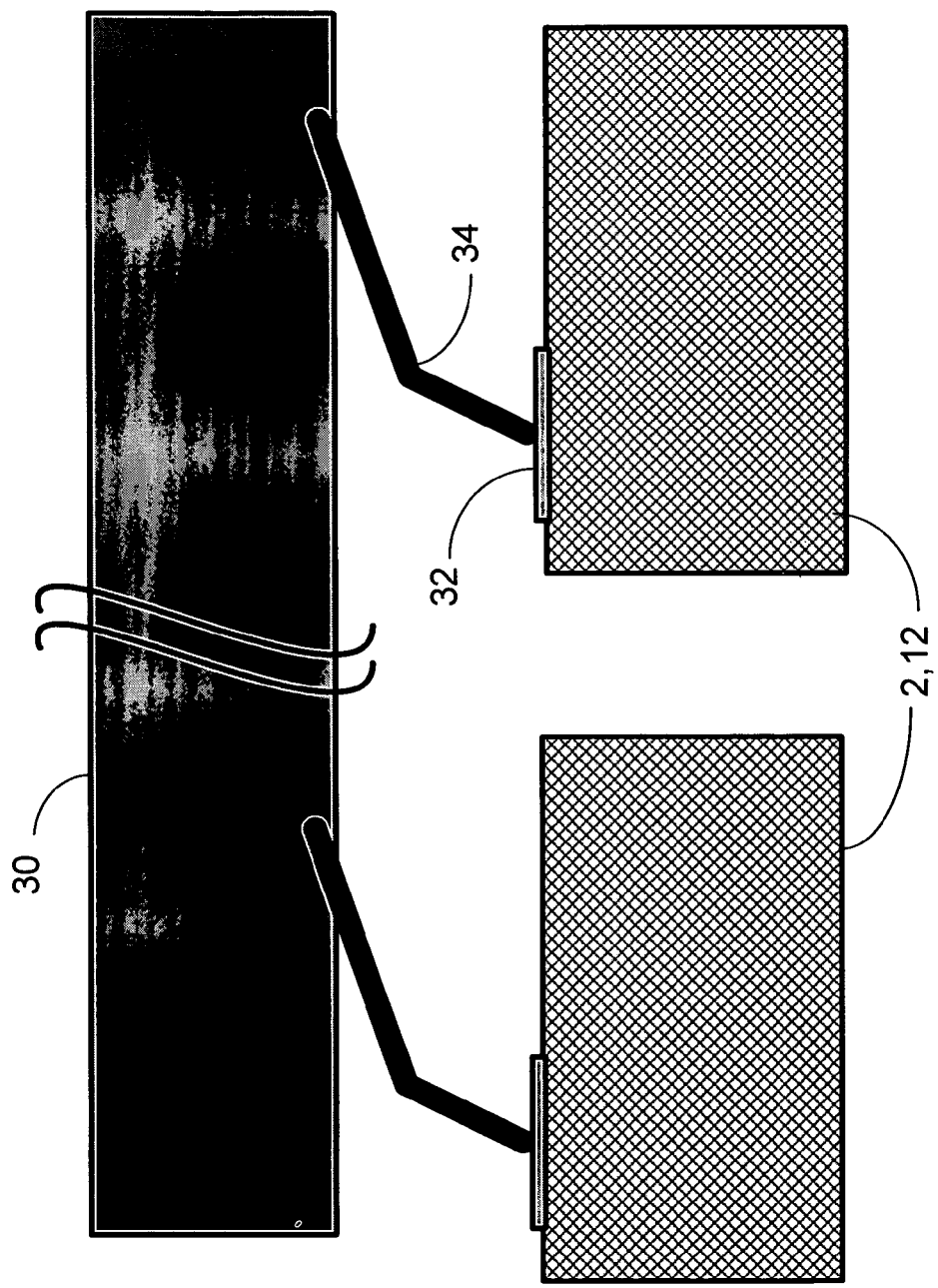
FIG. 4 is a side detail view of a probe card as used in a system for testing an array of electronic components, the probe being in a downward position to engage the components.

Many variations of this shunting circuit and the activation switch mechanism are possible. FIGS. 2–4 show an embodiment in which a probe card 30 is used as part of the testing circuit 6 with an array of electronic components 12, where again, sliders 2 are used as examples. Sliders 2 are configured with electrical connection sites, known as reader pads 32 to which probes 34 from the probe card 30 can be placed in contact during the Quasi-Static Measurement phase. The probe card 30 preferably moves up and down in order to make contact or break contact between the probes 34 and the reader pads 32, as shown by FIG. 3. When the sliders 2 are loaded into a testing array, the probe 30 is initially up and the protection circuit (see FIG. 1) is activated for the stress-testing phase. Then, at desired intervals, the protection circuit 10 is switched off, the probe card 30 descends so that the probes 34 make contact with the reader pads 32, and the Quasi Static Measurement phase begins. When it is complete, the probe card 30 moves up, breaking contact with the sliders 2 and the protection circuit 10 is switched on again, if another stress testing cycle is desired.

An embodiment of the actuator 26 is shown in more detail in FIG. 5. Although this mechanism is subject to much variation, this actuator 40 is activated electrically, magnetically or pneumatically to activate or deactivate a number of switches 24 to a number of protection circuits 10 in a number of component arrays (not shown). Although not limited to this configuration, the actuator 40 is preferably a solenoid 42 attached to a nonconductive rod 44 which is then attached to each mechanical switch 24 such that they are "ganged together". Since minimizing ESD is a major concern, the actuator 40 preferably includes an electromagnetic interference (EMI) shield 46 which prevents EMI emission when the actuator 40 is turned on or off. The non-conductive rod 44 further insures against production of ESD.

While the present invention has been shown and described with regard to certain preferred embodiments, it is to be understood that modifications in form and detail will no doubt be developed by those skilled in the art upon reviewing this disclosure. It is therefore intended that the following claims cover all such alterations and modifications that nevertheless include the true spirit and scope of the inventive features of the present invention.

What is claimed is:

1. A method for minimizing damage from electrostatic discharge (ESD) during long-term testing of electronic components and assemblies, the method comprising:
   A) conducting a stress-test, during which a protection circuit which includes back-to-back diodes, a resistor and a capacitor in parallel with said electronic components and assemblies, is engaged which shields said components and assemblies from ESD; and
   B) conducting at least one functional test during said stress-test, at which time, said protection circuit is disengaged.

2. The method of claim 1, wherein:
said stress-test is conducted by applying a bias current to said components and assemblies.

3. The method of claim 1, wherein:
said protection circuit is connected to shunt ESD away from said components and assemblies.

4. The method of claim 1, wherein:
said protection circuit is engaged and disengaged by use of a mechanical switch.

5. The method of claim 1, wherein:
said functional testing includes Quasi-Static testing, in which uniform fields are applied to each head/device for magnetic performance evaluations.

6. A system for conducting long-term testing of electronic components and assemblies while providing protection from ESD, said system comprising:
   a testing circuit for providing current to said components and assemblies during long-term testing which includes at least one stress-testing phase and at least one functional testing phase;
   at least one protection circuit for protecting said components and assemblies during said stress-testing phase of said long-term testing and said protection circuit includes back-to-back diodes, a resistor and a capacitor in parallel with said testing circuit; and
   means for disengaging said at least one protection circuit from said components and assemblies during said functional testing phase of said long-term testing.

7. The system of claim 6, wherein:
said stress-testing phase is conducted by applying a bias current to said components and assemblies.

8. The system of claim 6, wherein:
said at least one protection circuit is connected to shunt ESD away from said components and assemblies.

9. The system of claim 6, wherein:
said means for disengaging said at least one protection circuit includes a means for engaging said protection circuit when stress-testing is resumed.

10. The system of claim 9, wherein:
said means for disengaging said at least one protection circuit and said means for engaging said protection circuit is a mechanical switch.

11. The system of claim 6, wherein:
said testing circuit includes a probe card having probes for supplying current to a plurality of components and assemblies during said functional testing phase.

12. The system of claim 11, wherein:
said probe card is disengaged from contact with said plurality of components and assemblies during said stress testing phase.

13. The system of claim 6, wherein:
said means for disengaging includes an actuator which is connected to at least one mechanical switch.

14. A system for conducting long-term testing of electronic components and assemblies while providing protection from ESD, said system comprising:
   a testing circuit for providing current to said components and assemblies during long-term testing which includes at least one stress-testing phase and at least one functional testing phase;
   at least one protection circuit for protecting said components and assemblies during said stress-testing phase of said long-term testing; and
   means for disengaging said at least one protection circuit from said components and assemblies during said functional testing phase of said long-term testing, where said means for disengaging includes an actuator which is connected to at least one mechanical switch and said actuator is connected to a plurality of mechanical switches by a non-conductive rod.

15. The system of claim 14, wherein:
said protection circuit includes back-to-back diodes, a resistor and a capacitor in parallel with said testing circuit.

16. A system for conducting long-term testing of electronic components and assemblies while providing protection from ESD, said system comprising:
   a testing circuit for providing current to said components and assemblies during long-term testing which includes at least one stress-testing phase and at least one functional testing phase;
   at least one protection circuit for protecting said components and assemblies during said stress-testing phase of said long-term testing;
   means for disengaging said at least one protection circuit from said components and assemblies during said functional testing phase of said long-term testing, where said means for disengaging includes an actuator which is connected to at least one mechanical switch; and
   said actuator is a solenoid, and includes an EMI shield to protect components from ESD.

17. The system of claim 16, wherein:
said protection circuit includes back-to-back diodes, a resistor and a capacitor in parallel with said testing circuit.

* * * * *